US010520512B2

(12) United States Patent
Bergmann et al.

(10) Patent No.: US 10,520,512 B2
(45) Date of Patent: Dec. 31, 2019

(54) METHOD FOR PREDICTING THE RISK OF A SUBJECT FOR CONTRACTING DIABETES MELLITUS AND/OR METABOLIC SYNDROME OR FOR DIAGNOSING METABOLIC SYNDROME IN A SUBJECT

(71) Applicant: Sphingotec GmbH, Henningsdorf (DE)

(72) Inventors: Andreas Bergmann, Berlin (DE); Olle Melander, Malmoe (SE)

(73) Assignee: SPHINGOTEC GMBH, Hennigsdorf (DE)

(*) Notice: Subject to any disclaimer, the term of this patent is extended or adjusted under 35 U.S.C. 154(b) by 0 days.

(21) Appl. No.: 14/383,422

(22) PCT Filed: Mar. 8, 2013

(86) PCT No.: PCT/EP2013/054801
§ 371 (c)(1),
(2) Date: Sep. 5, 2014

(87) PCT Pub. No.: WO2013/132090
PCT Pub. Date: Sep. 12, 2013

(65) Prior Publication Data
US 2015/0056203 A1 Feb. 26, 2015

Related U.S. Application Data

(60) Provisional application No. 61/608,350, filed on Mar. 8, 2012.

(30) Foreign Application Priority Data

Mar. 8, 2012 (EP) .................................... 12158680
Apr. 20, 2012 (EP) .................................... 12165062

(51) Int. Cl.
G01N 33/53 (2006.01)
G01N 33/68 (2006.01)

(52) U.S. Cl.
CPC . G01N 33/6893 (2013.01); G01N 2333/4706 (2013.01); G01N 2800/042 (2013.01)

(58) Field of Classification Search
CPC .................................................. G01N 33/6893
See application file for complete search history.

(56) References Cited

U.S. PATENT DOCUMENTS

| 5,430,047 | A | 7/1995 | Johnson et al. | |
| 6,248,527 | B1* | 6/2001 | Chen .................. | A61K 38/4813 435/6.11 |
| 9,217,747 | B2* | 12/2015 | McKenna .............. | G01N 33/66 |
| 2004/0023334 | A1 | 2/2004 | Prior | |
| 2008/0280306 | A1* | 11/2008 | Ernst ....................... | G01N 33/74 435/7.1 |
| 2009/0012716 | A1* | 1/2009 | Urdea .............. | G01N 33/48714 702/19 |
| 2010/0028995 | A1 | 2/2010 | Graversen et al. | |
| 2011/0305633 | A1 | 12/2011 | Forgez et al. | |

FOREIGN PATENT DOCUMENTS

| EP | 0 289 287 A2 | 11/1988 |
| EP | 0 353 971 A2 | 2/1990 |
| EP | 1 266 025 B1 | 11/2006 |
| EP | 2 314 308 A1 | 4/2011 |
| EP | 1 941 867 B1 | 10/2011 |
| EP | 2 231 860 B1 | 10/2011 |
| WO | WO 2005/040229 A1 | 5/2005 |
| WO | WO 2010/060748 A1 | 6/2010 |
| WO | WO 2011/023685 A1 | 3/2011 |
| WO | WO 2011/073214 A2 | 6/2011 |
| WO | WO 2011/154420 A2 | 12/2011 |

OTHER PUBLICATIONS

Quirion, et al. "Selective Blockade of Neurotensin-Induced Coronary Vessel Constriction in Perfused Rat Hearts by a Neurotensin Analogue", European Journal of Pharmacology, 61, 1980, pp. 309-312, (Four (4) pages).
International Search Report (PCT/ISA/210) dated Jul. 26, 2013 (Five (5) pages).
Written Opinion (PCT/ISA/237) dated Jul. 26, 2013 (Nine (9) pages).
Ernst, et al., "Proneurotensin 1-117, a stable neurotensin precursor fragment identified in human circulation", Peptides 27, 2006, vol. 27, No. 7, pp. 1787-1793, XP027957440, (Seven (7) pages).
Carraway, et al., "Radioimmunoassay for Neurotensin, a Hypothalamic Peptide", The Journal of Biological Chemistry, vol. 251, No. 22, 1976, pp. 7035-7044, XP055071491 (Eleven (11) pages).
Fernstrom, et al., "Immunoreactive Neurotensin Levels in Pancreas: Elevation in Diabetic Rats and Mice", Metabolism, vol. 30, No. 9, 1981, pp. 853-855, XP026313131, (Four (4) pages).
Watanabe, et al., "Metabolic syndrome and gastrointestinal diseases", Journal of Gastroenterology, vol. 42, No. 4, 2007, pp. 267-274, XP019518750, (Eight (8) pages).
Wolosin, et al., "Diabetes and the Gastrointestinal Tract", Clinical Diabetes, vol. 18, No. 4, 2000, pp. 148-151, XP002703335, (Seven (7) pages).

(Continued)

Primary Examiner — Mark Halvorson
(74) Attorney, Agent, or Firm — Millen White Zelano and Branigan, PC

(57) ABSTRACT

Subject matter of the present invention is a method for predicting the risk of a subject for contracting diabetes mellitus and/or metabolic syndrome or for diagnosing metabolic syndrome in a subject wherein said subject is non-diabetic, comprising the following steps determining the level of pro-neurotensin or fragments thereof of at least 5 amino acids in a bodily fluid obtained from said subject; and correlating said level of pro-neurotensin or fragments thereof with the risk of said subject for contracting diabetes mellitus and/or metabolic syndrome, wherein an elevated level is predictive for an enhanced risk of getting diabetes mellitus and/or metabolic syndrome, or wherein an elevated level correlates to the diagnosis of metabolic syndrome in a subject wherein said subject is non-diabetic.

Figure 1:
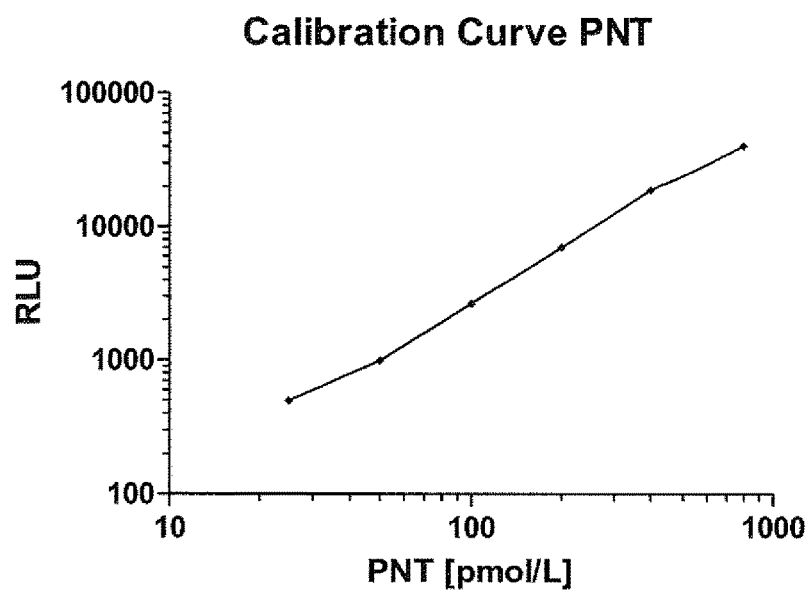

8 Claims, 2 Drawing Sheets
Specification includes a Sequence Listing.

(56) References Cited

OTHER PUBLICATIONS

Melander O. et al., "Plasma Proneurotensin and Incidence of Diabetes, Cardiovascular Disease, Breast Cancer, and Mortality", JAMA, vol. 308, No. 14, 2012, pp. 1469-1475, XP009165659, (Seven (7) pages).

Pichon, et al., "Serum Cholecystokinin and Neurotensin During Follow-Up of Pancreas, Prostate and Medullary Thyroid Tumors", Anticancer Research, vol. 19, No. 2B, 1999, pp. 1445-1450, (Eight (8) pages).

Meggiato, et al., "Serum Neurotensin in Human Pancreatic Cancer", Tumori: A Journal of Experimental and Clinical Oncology, vol. 82, No. 6, 1996, pp. 592-595, (Five (5) pages).

Enhoerning, et al., "Epidemiology and Prevention: Plasma Copeptin and the Risk of Diabetes Mellitus", Circulation, vol. 121, 2010, pp. 2102-2108, (Seven (7) pages).

Lane "A Short-Duration Polyethylene Glycol Fusion Technique for Increasing Production of Monoclonal Anti-body-Secreting Hybridomas", Journal of Immunological Methods, vol. 81, 1985, pp. 223-228, (Six (6) pages).

Marx, et al., "Monoclonal Antibody Production", ATLA, vol. 25, 1997, pp. 121-137, (Seventeen (17) pages).

\* cited by examiner

METHOD FOR PREDICTING THE RISK OF A SUBJECT FOR CONTRACTING DIABETES MELLITUS AND/OR METABOLIC SYNDROME OR FOR DIAGNOSING METABOLIC SYNDROME IN A SUBJECT

SEQUENCE LISTING

The instant application contains a Sequence Listing which has been submitted electronically in ASCII format and is hereby incorporated by reference in its entirety. Said ASCII copy, created on Jan. 30, 2018, is named Boehmerp-0240_SL.txt and is 8,131 bytes in size.

Subject matter of the present invention is a method for predicting the risk of a subject for contracting diabetes mellitus and/or metabolic syndrome or for diagnosing metabolic syndrome in a subject wherein said subject is non-diabetic, comprising the following steps:
- determining the level of pro-neurotensin or fragments thereof of at least 5 amino acids in a bodily fluid obtained from said subject; and
- correlating said level of pro-neurotensin or fragments thereof with the risk of said subject for contracting diabetes mellitus and/or metabolic syndrome, wherein an elevated level is predictive for an enhanced risk of getting diabetes mellitus and/or metabolic syndrome, or wherein an elevated level correlates to the diagnosis of metabolic syndrome in a subject wherein said subject is non-diabetic.

The term "elevated level" means a level above a certain threshold level.

Neurotensin is a 13-amino acid neuropeptide derived from the prepro-neurotensin precursor and stochiometrically released together with the stable 117-amino acid peptide pro-neurotensin (P-NT) and the mature hormone binds to three different receptors, neurotensin receptor 1 and 2 (Ntsr1 and Ntsr2), which are G-protein coupled receptors and neurotensin receptor 3 (Ntsr3) which is non-G-protein coupled and also known as Sortillin-1 (SORT1).

Neurotensin is released peripherally from the small intestine as well as centrally from the hypothalamus. The peripheral secretion of neurotensin is stimulated by food-intake, especially by fat, and is known to regulate gastrointestinal motility and pancreatic and biliary secretion. Interestingly, neurotensin is implicated in appetite control as an anorectic hormone as it acutely reduces food intake following both central (intracerebroventricular) and peripheral (intraperitoneal) injection in rats, an effect which seems mainly mediated through the neurotensin-1 receptor (Ntsr1). In obese as compared to normal-weight human subjects, postprandial plasma neurotensin concentration was reduced following a liquid fatty meal (Widen et al 1992, Reg peptides; Plasma concentrations of regulatory peptides in obesity following modified sham feeding (MSF) and a liquid test meal), suggesting regulation of neurotensin secretion is disturbed in obesity. However, no large study has investigated if and how neurotensin is related to measures of obesity. Interestingly, P-NT significantly increases after gastric by-pass (Roux-en-Y), an operation shown to lead to normoglycemia in the majority of obese type II diabetes patients, but it is not known whether neurotensin is implicated in the development diabetes mellitus in general. Furthermore, the neurotensin system has been implicated in development of coronary artery disease and myocardial infarction as variation of the Ntsr3 (SORT1) gene is one of the strongest common coronary artery diseases susceptibility genes known in humans.

The mechanistic link between obesity and cancer is largely unknown, however, one of the dominating theories is that excess of fat deposits leads to increased peripheral aromatization of androgens and thus elevated circulating estrogen levels. In addition, one of the hallmarks of obesity, hyperinsulinemia, has been shown to inhibit hepatic production of Sexual Hormone Binding Globulin (SHBG), thus increasing bioavailable levels of both estrogens and androgens suggesting ways through which obesity may increase the risk of common forms of sex-hormone driven forms of cancer such as breast and prostate cancer. Interestingly, both neurotensin and Ntsr1 expression is common in malignant ductal breast cancer tumors and experimentally pharmacological blockade or RNA silencing of the NTSR1 reduces tumour growth in mice.

The level of expression of neurotensin receptor 1 (NTSR1) in breast cancer cells has been used for determining the prognosis of a subject suffering from breast cancer (US 2011/0305633). Further, it is stated in by the same authors that no clear correlation has been described today between circulating neurotensin and the stages of pancreas, prostate, or medullar thyroid tumors probably due to rapid clearance by the liver. Interestingly, it was found that in a series of 51 patients with invasive ductal breast cancer 91% of all tumors were positive for neurotensin receptor 1 (NTSR1) but only 31% of all tumors were positive for neurotensin in said tissue. (Souaze et. al. Cancer Research 2006; 66: (12) pages 6243-6249).

There is some evidence that neurotensin and neurotensin receptors participate in cancer growth, in particular in lung cancer, pancreatic cancer and colon cancer (Carraway et al.; Peptides 27 (2006) 2445-2460). It has been reported that levels of NT in sera of patients with pancreatic cancer were significantly enhanced (Picheon et al, Anticancer Research 1999; 19; 1445-50). Interestingly this group found that NT levels fell with progression of the disease for both prostate an pancreatic cancer. In contrast, thereto, Meggiato et al.; Tumori 1996; 82; 592-5; found that plasma levels of NT were normal in pancreatic cancer but elevated in case where pancreatitis was diagnosed.

The use of copeptin for prediction of diabetes has been reported by Enhörning et al, *Circulation*. 2010; 121:2102-2108

A subject of the present invention was to investigate the prognostic and diagnostic power of NT for predicting the risk of a subject for contracting diabetes mellitus and/or metabolic syndrome or for diagnosing metabolic syndrome in a subject wherein said subject is non-diabetic. To address this issue, we measured stable fragments of pro-neurotensin in fasting plasma in said Swedish prospective cohort study (Malmö Diet and Cancer Study) and related baseline level of this biomarker to diabetes incidence during 15 years of follow-up.

Subject matter of the present invention is a method for predicting the risk of a subject for contracting diabetes mellitus and/or metabolic syndrome or for diagnosing metabolic syndrome in a subject wherein said subject is non-diabetic, comprising the following steps:
- determining the level of pro-neurotensin or fragments thereof of at least 5 amino acids in a bodily fluid obtained from said subject; and
- correlating said level of pro-neurotensin or fragments thereof with the risk of said subject for contracting diabetes mellitus and/or metabolic syndrome, wherein an elevated level is predictive for an enhanced risk of getting diabetes mellitus and/or metabolic syndrome, or wherein an elevated level correlates to the diagnosis of metabolic syndrome in a subject wherein said subject is non-diabetic.

Subject matter of the present invention is a method for predicting the risk of a subject for contracting diabetes mellitus and/or metabolic syndrome or for diagnosing metabolic syndrome in a subject wherein said subject is non-diabetic, comprising the following steps:

determining the level of pro-neurotensin 1-117 or fragments thereof of at least 5 amino acids or pro-neurotensin 1-117 comprising peptides in a bodily fluid obtained from said subject; and correlating said level of pro-neurotensin 1-117 or fragments thereof or pro-neurotensin 1-117 comprising peptides with the risk of said subject for contracting diabetes mellitus and/or metabolic syndrome, wherein an elevated level is predictive for an enhanced risk of getting diabetes mellitus and/or metabolic syndrome, or wherein an elevated level correlates to the diagnosis of metabolic syndrome in a subject wherein said subject is non-diabetic.

The term "subject" as used herein refers to a living human or non-human organism. Preferably herein the subject is a human subject. In a specific embodiment of the invention said subject is a female subject. In a specific embodiment of the invention said subject is non-IFG (non-prediabetic) subject.

In one embodiment of the invention the level of pro-neurotensin or fragments thereof of at least 5 amino acids or pro-neurotensin 1-117 comprising peptides in a bodily fluid is the fasting level of pro-neurotensin or fragments thereof of at least 5 amino acid or pro-neurotensin 1-117 comprising peptides. Fasting level means no food uptake 12 h prior blood sampling.

The level of pro-neurotensin 1-117 or fragments thereof of at least 5 amino acids or pro-neurotensin 1-117 comprising peptides in a bodily fluid obtained from said female subject that is predictive for the risk of for contracting diabetes mellitus and/or metabolic syndrome is released from the small intestine. The release of neurotensin from the small intestine is stimulated by food intake, especially by fat, and is known to regulate gastrointestinal motility and pancreatic and biliary secretion. Pro-neurotensin 1-117 and fragments thereof or pro-neurotensin 1-117 comprising peptides are used as a surrogate marker for the released neurotensin as neurotensin and pro-neurotensin 1-117 and fragments thereof or pro-neurotensin 1-117 comprising peptides are released in equimolar amounts from pro-neurotensin.

It is the surprising finding of the present invention that the peripheral secretion of neurotensin/pro-neurotensin 1-117 or fragments thereof of at least 5 amino acids or pro-neurotensin 1-117 comprising peptides is indicative for the susceptibility of a female subject to for contracting diabetes mellitus and/or metabolic syndrome. Thus, dietary measures as reduction of fat uptake may lower said risk in said subject.

The correlation between the level of pro-neurotensin or fragments thereof of at least 5 amino acids or PNT 1-117 comprising peptides in a bodily fluid obtained from said subject and the risk of contracting diabetes mellitus and/or metabolic syndrome is continuous, i.e. the higher the level the higher the risk.

For the sake of practicability the person skilled in the art may use threshold(s).

Thus, the term "elevated level" may mean a level above a threshold level.

A bodily fluid may be selected from the group comprising blood, serum, plasma, urine, csf, and saliva.

The present data suggest a strong correlation between the level of pro-neurotensin or fragments thereof, especially pro-neurotensin 1-117 or fragments thereof or pro-neurotensin 1-117 comprising peptides with diabetes, in particular in subjects with no prevalent diabetes.

The present data also suggest a strong correlation between the level of pro-neurotensin or fragments thereof, especially pro-neurotensin 1-117 or fragments thereof or pro-neurotensin 1-117 comprising peptides with diabetes, in hypertensive subjects, which is a common high-risk group for cardiovascular disease and/or diabetes.

Fragments of pro-neurotensin that may be determined in a bodily fluid may be e.g.

```
(Pro-neurotensin 1-147)
                                         SEQ ID NO: 1
SDSEEEMKAL EADFLTNMHT SKISKAHVPS WKMTLLNVCS
LVNNLNSPAE ETGEVHEEEL VARRKLPTAL DGFSLEAMLT
IYQLHKICHS RAFQHWELIQ EDILDTGNDK NGKEEVIKRK
IPYILKRQLY ENKPRRPYIL KRDSYYY (pro-neurotensin 1-125 (large neuromedin N))
                                         SEQ ID NO: 2
SDSEEEMKAL EADFLTNMHT SKISKAHVPS WKMTLLNVCS
LVNNLNSPAE ETGEVHEEEL VARRKLPTAL DGFSLEAMLT
IYQLHKICHS RAFQHWELIQ EDILDTGNDK NGKEEVIKR
KIPYIL (neuromedin N:)
                                         SEQ ID NO: 3
KIPYIL (neurotensin)
                                         SEQ ID NO: 4
pyroQLYENKPRRP YIL (pro-neurotensin 1-117)
                                         SEQ ID NO: 5
SDSEEEMKAL EADFLTNMHT SKISKAHVPS WKMTLLNVCS
LVNNLNSPAE ETGEVHEEEL VARRKLPTAL DGFSLEAMLT
IYQLHKICHS RAFQHWELIQ EDILDTGNDK NGKEEVI (pro-neurotensin 1-132)
                                         SEQ ID NO: 6
SDSEEEMKAL EADFLTNMHT SKISKAHVPS WKMTLLNVCS
LVNNLNSPAE ETGEVHEEEL VARRKLPTAL DGFSLEAMLT
IYQLHKICHS RAFQHWELIQ EDILDTGNDK NGKEEVIKRK
IPYILKRQLY EN (Pro-Neurotensin 1-125)
                                         SEQ ID No 7:
SDSEEEMKAL EADFLTNMHT SKISKAHVPS WKMTLLNVCS
LVNNLNSPAE ETGEVHEEEL VARRKLPTAL DGFSLEAMLT
IYQLHKICHS RAFQHWELIQ EDILDTGNDK NGKEEVIKRK
IPYIL (pro-neurotensin 120-140)
                                         SEQ ID NO: 8
KIPYILKRQL YENKPRRPYI L (pro-neurotensin 120-147)
                                         SEQ ID NO: 9
KIPYILKRQL YENKPRRPYIL KRDSYYY (pro-neurotensin 128-147)
                                         SEQ ID NO: 10
QLYENKPRRP YILKRDSYYY
```

In a more specific embodiment of the method according to the present invention the level of pro-neurotensin 1-117 is determined.

In a specific embodiment the level of pro-neurotensin, especially pro-neurotensin 1-117 or fragments thereof or pro-neurotensin 1-117 comprising peptides, is measured with an immunoassay. More specifically an immunoassay is used as described in Ernst et al. Peptides 27 (2006) 1787-1793.

An immunoassay that may be useful for determining the level of pro-neurotensin or fragments thereof of at least 5 amino acids or pro-neurotensin 1-117 comprising peptide may comprise the steps at outlines in example 2. All thresholds and values have to be seen in light of the test and the calibration used according to Example 2. A person skilled in the art may know that the absolute value of a threshold might be influenced by the calibration used. This means that all values and thresholds given herein are to be understood in context of the calibration used in herein (Example 2). A human P-NT-calibrator is available by ICI-Diagnostics, Berlin, Germany. Alternatively, the assay may be calibrated by synthetic or recombinant P-NT 1-117 or fragments thereof (see also Ernst et. al, 2006).

The threshold for determining the risk of a subject for contracting diabetes mellitus and/or metabolic syndrome or for diagnosing metabolic syndrome in a subject wherein said subject is non-diabetic according to the methods of the present invention is above 78 pmol/l PNT, preferred 100 pmol/l, more preferred 150 pmol/l. In a specific embodiment said threshold is about 100 pmol/l. These thresholds are related to the above mentioned calibration method. A pro-NT value above said threshold means that the subject has an enhanced risk of contracting diabetes mellitus and/or metabolic syndrome.

The definition of diabetes is as follows: a history of physiciane diagnosis or being on anti-diabetic medication or having a fasting whole blood glucose >/=6.1 mmol/l (note this is =7.0 mmol/l in plasma) at the baseline examination.

Pre-diabetes, impaired fasting glucose (IFG): IFG=fasting plasma glucose of 6.1-6.9 mmol/l.

The definition of normotensive/high blood pressure (HBP) is as follows:

HBP: Systolic BP>/=140 mmHg or Diastolic BP>/=90 mmHg or being on antihypertensive medications. Subjects having normal blood pressure (BP) are all other subjects, i.e subjects with systolic BP<140 mmHg or Diastolic BP<90 mmHg or not being on antihypertensive medications.

In a specific embodiment of the method according to the invention said subject is a non-diabetic with fasting blood glucose of less than 6.1 mmol/l but more than 5.4 mmol/1.

In a specific embodiment of the method according to the invention said subject is a non-diabetic subject with fasting blood glucose of equal or less than 5.4 mmol/l.

In a specific embodiment of the method according to the invention said the risk of the subject for developing diabetes mellitus type II is determined.

In a specific embodiment of the method according to the invention the prediction of the risk of the subject for contracting diabetes mellitus and/or metabolic syndrome or the diagnosis of metabolic syndrome is improved by additionally determining and using the level of at least one laboratory parameter or further marker selected from the group comprising fasting blood or plasma glucose, triglycerides, HDL cholesterol or subfractions thereof, LDL cholesterol or subfractions thereof, cystatin C, insulin, CRP, vasopressin or its precursors or fragments thereof and BNP or its precursors or fragments thereof.

In a specific embodiment of the method according to the invention additionally at least one clinical parameter is determined selected from the group comprising age, gender, systolic blood pressure, diastolic blood pressure, antihypertensive treatment (AHT), body mass index, waist circumference, waist-hip-ratio, current smoker, diabetes heredity and previous cardiovascular disease (CVD).

A further embodiment of the invention is a method for predicting the risk of a subject for contracting diabetes mellitus and/or metabolic syndrome or for diagnosing metabolic syndrome in a subject wherein said subject is non-diabetic according to any of the preceding claims, wherein the level of pro-neurotensin or fragments thereof either alone or in conjunction with other prognostically useful laboratory or clinical parameters is used for the prediction of the risk of a subject for contracting diabetes mellitus and/or metabolic syndrome or for the diagnosis of metabolic syndrome by a method which may be selected from the following alternatives:

- comparison with the median of the level of pro-neurotensin or fragments thereof or pro-neurotensin 1-117 comprising peptides in an ensemble of pre-determined samples in a population of apparently healthy subjects,
- comparison with a quantile of the level of pro-neurotensin or fragments thereof or pro-neurotensin 1-117 comprising peptides in an ensemble of pre-determined samples in a population of apparently healthy subjects,
- calculation based on Cox Proportional Hazards analysis or by using Risk index calculations such as the NRI (Net Reclassification Index) or the IDI (Integrated Discrimination Index).

In one embodiment of the invention the sample is selected from the group comprising blood sample, a serum sample, a plasma sample, a cerebrospinal fluid sample, a saliva sample and a urine sample or an extract of any of the aforementioned samples. In a specific embodiment of the method according to the invention the level of pro-neurotensin or fragments thereof or pro-neurotensin 1-117 comprising peptide having at least a length of 5 amino acids is determined by a diagnostic assay, preferably by an immunoassay.

In a specific embodiment of the method according to the invention the method is performed more than once in order to monitor the risk of getting diabetes mellitus and/or metabolic syndrome or in order to monitor the course of treatment of metabolic syndrome in a subject wherein said subject is non-diabetic.

In a specific embodiment of the method according to the invention said monitoring is performed in order to evaluate the response of said subject to preventive and/or therapeutic measures taken.

In a specific embodiment of the method according to the invention the method is used in order to stratify said subjects into risk groups.

Also encompassed by the present invention is a point-of-care device for performing a method according to the invention.

Also encompassed by the present invention is an assay and/or kit for performing a method according to the invention.

Subject matter of the invention is also a binder to neurotensin or to a neurotensin receptor, for the use in prevention or therapy diabetes mellitus and/or metabolic syndrome in a subject.

In one embodiment of the invention the binder reduces the bioactivity of neurotensin to 70% or less.

According to the invention the binder to neurotensin is selected from the group consisting of antibodies e.g. IgG, a typical full-length immunoglobulin, or antibody fragments containing at least the F-variable domain of heavy and/or light chain as e.g. chemically coupled antibodies (fragment antigen binding) including but not limited to Fab-fragments including Fab minibodies, single chain Fab antibody, monovalent Fab antibody with epitope tags, e.g. Fab-V5Sx2; bivalent Fab (mini-antibody) dimerized with the CH3 domain; bivalent Fab or multivalent Fab, e.g. formed via multimerization with the aid of a heterologous domain, e.g.

via dimerization of dHLX domains, e.g. Fab-dHLX-FSx2; F(ab')2-fragments, scFv-fragments, multimerized multivalent or/and multispecific scFv-fragments, bivalent and/or bispecific diabodies, BITE® (bispecific T-cell engager), trifunctional antibodies, polyvalent antibodies, e.g. from a different class than G; single-domain antibodies, e.g. nanobodies derived from camelid or fish immunoglobulines.

According to the invention the binder to a neurotensin receptor is selected from the group consisting of antibodies e.g. IgG, a typical full-length immunoglobulin, or antibody fragments containing at least the F-variable domain of heavy and/or light chain as e.g. chemically coupled antibodies (fragment antigen binding) including but not limited to Fab-fragments including Fab minibodies, single chain Fab antibody, monovalent Fab antibody with epitope tags, e.g. Fab-V5Sx2; bivalent Fab (mini-antibody) dimerized with the CH3 domain; bivalent Fab or multivalent Fab, e.g. formed via multimerization with the aid of a heterologous domain, e.g. via dimerization of dHLX domains, e.g. Fab-dHLX-FSx2; F(ab')2-fragments, say-fragments, multimerized multivalent or/and multispecific scFv-fragments, bivalent and/or bispecific diabodies, BITE® (bispecific T-cell engager), trifunctional antibodies, polyvalent antibodies, e.g. from a different class than G; single-domain antibodies, e.g. nanobodies derived from camelid or fish immunoglobulines, or a peptide antagonist e.g. [D-Trp$^{11}$]-Neurotensin, [Tyr(Me)$^{11}$]-Neurotensin (e.g. described by Quiron et al.), or a non-peptide antagonist, e.g. Levocabastine, SR-48692 (NTS1 selective), SR-142948 (unselective), SR-142948A, CP 96345, [3H]SR-48692, SR 48692, SR-48527 and SR-49711, or a binder scaffold e.g. tetranectin-based non-Ig scaffolds (e.g. described in US 2010/0028995), fibronectin scaffolds (e.g. described in EP 1266 025; lipocalin-based scaffolds ((e.g. described in WO 2011/154420); ubiquitin scaffolds (e.g. described in WO 2011/073214), transferring scaffolds (e.g. described in US 2004/0023334), protein A scaffolds (e.g. described in EP 2231860), ankyrin repeat based scaffolds (e.g. described in WO 2010/060748), microproteins preferably microproteins forming a cystine knot) scaffolds (e.g. described in EP 2314308), Fyn SH3 domain based scaffolds (e.g. described in WO 2011/023685) EGFR-A-domain based scaffolds (e.g. described in WO 2005/040229) and Kunitz domain based scaffolds (e.g. described in EP 1941867).

EXAMPLES

Example 1

Development of Antibodies

Peptides/Conjugates for Immunization:
Peptides for immunization were synthesized (JPT Technologies, Berlin, Germany) with an additional N-terminal Cystein residue for conjugation of the peptides to Bovine Serum Albumin (BSA). The peptides were covalently linked to BSA by using Sulfo-SMCC (Perbio-science, Bonn, Germany). The coupling procedure was performed according to the manual of Perbio.

Labelled antibody (LA) peptide (P-NT 1-19):
H-CSDSEEEMKALEADFLTNMH-NH2 (SEQ ID NO: 11)
Solid phase antibody (SPA) peptide (P-NT 44-62):
H-CNLNSPAEETGEVHEEELVA-NH2 (SEQ ID NO: 12)
The antibodies were generated according to the following method:
A BALB/c mouse were immunized with 100 µg Peptide-BSA-Conjugate at day 0 and 14 (emulsified in 100 µl complete Freund's adjuvant) and 50 µg at day 21 and 28 (in 100 µl incomplete Freund's adjuvant). Three days before the fusion experiment was performed, the animal received 50 µg of the conjugate dissolved in 100 µl saline, given as one intraperitoneal and one intra venous injection.

Splenocytes from the immunized mouse and cells of the myeloma cell line SP2/0 were fused with 1 ml 50% polyethylene glycol for 30 s at 37° C. After washing, the cells were seeded in 96-well cell culture plates. Hybrid clones were selected by growing in HAT medium [RPMI 1640 culture medium supplemented with 20% fetal calf serum and HAT-Supplement]. After two weeks the HAT medium is replaced with HT Medium for three passages followed by returning to the normal cell culture medium.

The cell culture supernatants were primary screened for antigen specific IgG antibodies three weeks after fusion. The positive tested microcultures were transferred into 24-well plates for propagation. After retesting the selected cultures were cloned and recloned using the limiting-dilution technique and the isotypes were determined.

(Lane, R. D. "A short-duration polyethylene glycol fusiontechnique for increasing production of monoclonal antibody-secreting hybridomas", J. Immunol. Meth. 81: 223-228; (1985), Ziegler, B. et al. "Glutamate decarboxylase (GAD) is not detectable on the surface of rat islet cells examined by cytofluorometry and complement-dependent antibody-mediated cytotoxicity of monoclonal GAD antibodies", Horm. Metab. Res. 28: 11-15, (1996)).

Monoclonal Antibody Production
Antibodies were produced via standard antibody production methods (Marx et al, Monoclonal Antibody Production, ATLA 25, 121, 1997,) and purified via Protein A-chromatography. The antibody purities were >95% based on SDS gel electrophoresis analysis.

Example 2

Immunoassay for the Quantification of Human Pro-Neurotensin

The technology used was a sandwich coated tube luminescence immunoassay, based on Akridinium ester labelling.

Labelled compound (tracer): 100 µg (100 µl) LA (1 mg/ml in PBS, pH 7.4, was mixed with 10 µl Akridinium NHS-ester (1 mg/ml in acetonitrile, InVent GmbH, Germany) (EP 0353971) and incubated for 20 min at room temperature. Labelled LA was purified by Gel-filtration HPLC on Bio-Sil SEC 400-5 (Bio-Rad Laboratories, Inc., USA) The purified LA was diluted in (300 mmol/l potassiumphosphate, 100 mmol/l NaCl, 10 mmol/l Na-EDTA, 5 g/l Bovine Serum Albumin, pH 7.0). The final concentration was approx. 800.000 relative light units (RLU) of labelled compound (approx. 20 ng labeled antibody) per 200 µl. Acridiniumester chemiluminescence was measured by using an AutoLumat LB 953 (Berthold Technologies GmbH & Co. KG).

Solid phase: Polystyrene tubes (Greiner Bio-One International AG, Austria) were coated (18 h at room temperature) with SPA (1.5 µg SPA/0.3 ml 100 mmol/l NaCl, 50 mmol/l TRIS/HCl, pH 7.8). After blocking with 5% bovine serum albumine, the tubes were washed with PBS, pH 7.4 and vakuum dried.

Calibration:
The assay was calibrated, using dilutions of P-NT-containing human serum. A pool of human sera with high P-NT-immunoreactivity (InVent Diagostika, Hennigsdorf, Germany) was diluted with horse serum (Biochrom AG, Deutschland) (assay standards).

The standards were calibrated by use of the human P-NT-calibrator (ICI-Diagnostics, Berlin, Germany). Alternatively, the assay may be calibrated by synthetic or recombinant P-NT 1-117 or fragments thereof (see also Ernst et al., 2006).

P-NT Immunoassay:

50 µl of sample (or calibrator) was pipetted into SPA coated tubes, after adding labelled LA (200 µl), the tubes were incubated for 16-22 h at 18-25° C. Unbound tracer was removed by washing 5 times (each 1 ml) with washing solution (20 mM PBS, pH 7.4, 0.1% Triton X-100).

Tube-Bound LA was Measured by Using the LB 953

FIG. 1 shows a typical P-NT dose/signal curve.

Example 3

Population Study

We measured P-NT in fasting plasma from 4362 participants of the population based Malmö Diet and Cancer Study baseline exam in 1991-1994 (men age 58±6 years and 59% females). We used multivariable adjusted (all traditional cardiovascular risk factors, diabetes risk factors and in analyses of cancer also heredity for cancer) Cox proportional hazards models to relate baseline P-NT (hazard ratio per each standard deviation increase of log-transformed P-NT) to the time to the first event of each of the studied endpoints during a median follow-up time of more than 12 years. Endpoints were retrieved through the Swedish National Hospital Discharge Registry, the Swedish Myocardial Infarction Registry, the Stroke in Malmö Registry and the Swedish Cancer Registry. Retrieval of endpoints through these registries has been validated and found to be accurate.

TABLE 1

Clinical characteristics of the total study population
Descriptive Statistics

|  | N | Mean | Std. Deviation |
|---|---|---|---|
| Age at MDCS screening | 4362 | 57.643 | 5.9797 |
| Systolic blood pressure (mmHg) | 4362 | 141.91 | 19.158 |
| Diastolic blood pressure (mmHg) | 4362 | 87.02 | 9.501 |
| body-mass-index (weight/kg×kg) | 4362 | 25.7642 | 3.91173 |
| WAIST (cm) | 4361 | 83.56 | 12.791 |
| Glucose (mmol/l) | 4362 | 5.1826 | 1.33736 |
| Triglycerides (mmol/l) | 4362 | 1.3142 | .63660 |
| High density lipoprotein (mmol/l) | 4362 | 1.3908 | .37068 |
| Low density lipoprotein (mmol/l) | 4362 | 4.1632 | .98774 |
| P-INSULIN | 4280 | 7.889 | 7.6975 |
| PNT [pmol/l] | 4362 | 123.01743 | 76.746549 |
| Valid N (listwise) | 4279 | | |

TABLE 2

Gender

|  |  | Frequency | Percent | Valid Percent | Cumulative Percent |
|---|---|---|---|---|---|
| Valid | male | 1803 | 413 | 41.3 | 41.3 |
|  | woman | 2559 | 58.7 | 58.7 | 100.0 |
|  | Total | 4362 | 100.0 | 100.0 |  |

TABLE 3

Q + Diary: Anti Hypertension Treatment (C02, C03, C07, C08, C09) at baseline according to questionnaire or diary book

|  |  | Frequency | Percent | Valid Percent | Cumulative Percent |
|---|---|---|---|---|---|
| Valid | No | 3684 | 84.5 | 84.5 | 84.5 |
|  | Yes | 678 | 15.5 | 15.5 | 100.0 |
|  | Total | 4362 | 100.0 | 100.0 |  |

TABLE 4

DIAB MELL (fb >6.0 or pos Q DM)

|  |  | Frequency | Percent | Valid Percent | Cumulative Percent |
|---|---|---|---|---|---|
| Valid | no | 3993 | 91.5 | 91.5 | 91.5 |
|  | yes | 369 | 8.5 | 8.5 | 100.0 |
|  | Total | 4362 | 100.0 | 100.0 |  |

TABLE 5 current_smoker0

|  |  | Frequency | Percent | Valid Percent | Cumulative Percent |
|---|---|---|---|---|---|
| Valid | .00 | 3212 | 73.6 | 73.6 | 73.6 |
|  | 1.00 | 1150 | 26.4 | 26.4 | 100.0 |
|  | Total | 4362 | 100.0 | 100.0 |  |

TABLE 6

Clinical characteristics of females in the study
Descriptive Statistics

|  | N | Mean | Std. Deviation |
|---|---|---|---|
| Age at MDCS screening | 2559 | 57.554 | 5.9403 |
| Systolic blood pressure (mm Hg) | 2559 | 140.50 | 19.311 |
| Diastolic blood pressure (mm Hg) | 2559 | 85.65 | 9.117 |
| body-mass-index (weight/kg×kg) | 2559 | 25.5196 | 4.19083 |
| WAIST (cm) | 2559 | 76.99 | 10.245 |
| Glucose (mmol/l) | 2559 | 5.0418 | 1.21798 |
| Triglycerides (mmol/l) | 2559 | 1.2245 | .58404 |
| High density lipoprotein (mmol/l) | 2559 | 1.5123 | .36949 |
| Low density lipoprotein (mmol/l) | 2559 | 4.2016 | 1.04762 |
| P-INSULIN | 2512 | 7.223 | 5.4223 |
| PNT (pmol/l) | 2559 | 125.60633 | 77.681673 |
| Valid N (listwise) | 2512 | | |

TABLE 7

Q + Diary: Anti Hypertension Treatment (C02, C03, C07, C08, C09) at baseline according to questionnaire or diary book

|  |  | Frequency | Percent | Valid Percent | Cumulative Percent |
|---|---|---|---|---|---|
| Valid | No | 2173 | 84.9 | 84.9 | 84.9 |
|  | Yes | 386 | 15.1 | 15.1 | 100.0 |
|  | Total | 2559 | 100.0 | 100.0 |  |

TABLE 8

DIAB MELL (fb >6.0 or pos Q DM)

|       |       | Frequency | Percent | Valid Percent | Cumulative Percent |
|-------|-------|-----------|---------|---------------|--------------------|
| Valid | no    | 2396      | 93.6    | 93.6          | 93.6               |
|       | yes   | 163       | 6.4     | 6.4           | 100.0              |
|       | Total | 2559      | 100.0   | 100.0         |                    |

TABLE 9 current_smoker0

|       |       | Frequency | Percent | Valid Percent | Cumulative Percent |
|-------|-------|-----------|---------|---------------|--------------------|
| Valid | .00   | 1906      | 74.5    | 74.5          | 74.5               |
|       | 1.00  | 653       | 25.5    | 25.5          | 100.0              |
|       | Total | 2559      | 100.0   | 100.0         |                    |

TABLE 10

Clinical characteristics of males in the study
Descriptive Statistics

|                                  | N    | Mean      | Std. Deviation |
|----------------------------------|------|-----------|----------------|
| Age at MDCS screening            | 1803 | 57.769    | 6.0345         |
| Systolic blood pressure (mmHg)   | 1803 | 143.90    | 18.766         |
| Diastolic blood pressure (mmHg)  | 1803 | 88.95     | 9.698          |
| body-mass-index (weight/kgxkg)   | 1803 | 26.1113   | 3.44882        |
| WAIST (cm)                       | 1802 | 92.89     | 9.932          |
| Glucose (mmol/l)                 | 1803 | 5.3825    | 1.46780        |
| Triglycerides (mmol/l)           | 1803 | 1.4416    | .68477         |
| High density lipoprotein (mmol/l)| 1803 | 1.2183    | .29669         |
| Low density lipoprotein (mmol/l) | 1803 | 4.1087    | .89336         |
| P-INSULIN                        | 1768 | 8.835     | 10.0090        |
| PNT (pmol/l)                     | 1803 | 119.34300 | 75.268054      |
| Valid N (listwise)               | 1767 |           |                |

TABLE 11

Q + Diary: Anti Hypertension Treatment (C02, C03, C07, C08, C09) at baseline according to questionnaire or diary book

|       |       | Frequency | Percent | Valid Percent | Cumulative Percent |
|-------|-------|-----------|---------|---------------|--------------------|
| Valid | No    | 1511      | 83.8    | 83.8          | 83.8               |
|       | Yes   | 292       | 16.2    | 16.2          | 100.0              |
|       | Total | 1803      | 100.0   | 100.0         |                    |

TABLE 12

DIAB MELL (fb >6.0 or pos Q DM)

|       |       | Frequency | Percent | Valid Percent | Cumulative Percent |
|-------|-------|-----------|---------|---------------|--------------------|
| Valid | no    | 1597      | 88.6    | 88.6          | 88.6               |
|       | yes   | 206       | 11.4    | 11.4          | 100.0              |
|       | Total | 1803      | 100.0   | 100.0         |                    |

TABLE 13 current_smoker0

|       |       | Frequency | Percent | Valid Percent | Cumulative Percent |
|-------|-------|-----------|---------|---------------|--------------------|
| Valid | .00   | 1306      | 72.4    | 72.4          | 72.4               |
|       | 1.00  | 497       | 27.6    | 27.6          | 100.0              |
|       | Total | 1803      | 100.0   | 100.0         |                    |

TABLE 14

QUARTILES OF PNT IN ALL:
PNT (pmol/l)

| Percentile Group of PNTpmol/l | N    | Median    | Minimum | Maximum  |
|-------------------------------|------|-----------|---------|----------|
| 1                             | 1091 | 60.22000  | 3.270   | 75.740   |
| 2                             | 1090 | 89.29000  | 75.790  | 104.600  |
| 3                             | 1092 | 122.67000 | 104.640 | 147.610  |
| 4                             | 1089 | 190.03000 | 147.660 | 1154.520 |
| Total                         | 4362 | 104.62000 | 3.270   | 1154.520 |

TABLE 15

QUARTILES OF PNT IN WOMEN:
PNT (pmol/l)

| Percentile Group of PNTpmol/l | N    | Median    | Minimum | Maximum  |
|-------------------------------|------|-----------|---------|----------|
| 1                             | 639  | 62.37000  | 5.100   | 78.580   |
| 2                             | 639  | 92.07000  | 78.610  | 108.770  |
| 3                             | 641  | 125.07000 | 108.960 | 150.000  |
| 4                             | 640  | 194.38500 | 150.050 | 1154.520 |
| Total                         | 2559 | 108.96000 | 5.100   | 1154.520 |

Quartile-concentrations were almost identical in all shown women subgroup analysis.

TABLE 16

QUARTILES OF PNT IN MEN:
PNT (pmol/l)

| Percentile Group of PNTpmol/l | N    | Median    | Minimum | Maximum  |
|-------------------------------|------|-----------|---------|----------|
| 1                             | 450  | 58.02000  | 3.270   | 70.800   |
| 2                             | 451  | 85.88000  | 70.970  | 98.820   |
| 3                             | 451  | 118.18000 | 98.880  | 143.940  |
| 4                             | 451  | 186.39000 | 144.180 | 1057.360 |
| Total                         | 1803 | 98.88000  | 3.270   | 1057.360 |

Quartile-concentrations were almost identical in all shown man subgroup analysis.

P-NT and Prediction of Diabetes Mellitus

Among subjects free from diabetes mellitus at baseline, 142 developed new-onset diabetes mellitus during a mean follow-up time of 12.7±2.2 years. After adjustment for baseline levels of all diabetes risk factors (age, gender, antihypertensive treatment, systolic blood pressure, body mass index, waist circumference, smoking, previous cardiovascular disease and fasting concentrations of blood glucose, triglycerides, insulin, HDL and LDL) each standard deviation (SD) increase of baseline P-NT conferred a hazard ratio (95% confidence interval) of 1.28 (1.09-1.50) (P=0.003) for the risk of new-onset diabetes. In a subgroup of subjects without pre-diabetes (Impaired Fasting Glucose, IFG), the hazards ratio for incident diabetes per 1 SD increase of P-NT was further increased: 1.48 (1.17-1.86) (P=0.001).

P-NT was independently associated with new-onset diabetes.

TABLE 17

TOTAL POPULATION (MALES AND FEMALES)
Variables in the Equation

| | B | SE | Wald | df | Sig. | Exp(B) | 95.0% CI for Exp(B) Lower | Upper |
|---|---|---|---|---|---|---|---|---|
| SEX | .748 | .296 | 6.404 | 1 | .011 | 2.112 | 1.184 | 3.770 |
| AGE | .004 | .015 | .058 | 1 | .809 | 1.004 | .974 | 1.034 |
| AHT_B | .385 | .197 | 3.807 | 1 | .051 | 1.470 | .998 | 2.165 |
| SBP_B | .003 | .005 | .297 | 1 | .586 | 1.003 | .993 | 1.012 |
| WAIST_B | .036 | .016 | 4.937 | 1 | .026 | 1.037 | 1.004 | 1.071 |
| BMI_B | −.010 | .041 | .053 | 1 | .817 | .991 | .914 | 1.074 |
| GLUCOS_B | 2.330 | .223 | 109.419 | 1 | .000 | 10.273 | 6.640 | 15.895 |
| HDL_B | −.625 | .310 | 4.063 | 1 | .044 | .535 | .292 | .983 |
| LDL_B | −.020 | .089 | .051 | 1 | .821 | .980 | .823 | 1.167 |
| LNINS | .023 | .185 | .016 | 1 | .900 | 1.024 | .712 | 1.471 |
| current_smoker0 | .311 | .190 | 2.692 | 1 | .101 | 1.365 | .941 | 1.981 |
| pr_cv_2008 | .062 | .450 | .019 | 1 | .891 | 1.063 | .440 | 2.570 |
| ZLN_PNT | .239 | .081 | 8.705 | 1 | .003 | 1.270 | 1.083 | 1.488 |

TABLE 18

FEMALES ONLY

Variables in the Equationb

| | B | SE | Wald | df | Sig. | Exp(B) | 95.0% CI for Exp(B) Lower | Upper |
|---|---|---|---|---|---|---|---|---|
| SEX | | | . | 0a | . | | | |
| AGE | .007 | .022 | .102 | 1 | .750 | 1.007 | .965 | 1.051 |
| AHT_B | .208 | .276 | .568 | 1 | .451 | 1.232 | .717 | 2.117 |
| SBP_B | −.001 | .007 | .011 | 1 | .918 | .999 | .986 | 1.013 |
| WAIST_B | .057 | .021 | 7.100 | 1 | .008 | 1.059 | 1.015 | 1.104 |
| BMI_B | −.062 | .055 | 1.269 | 1 | .260 | .940 | .845 | 1.047 |
| GLUCOS_B | 2.359 | .296 | 63.676 | 1 | .000 | 10.578 | 5.927 | 18.881 |
| HDL_B | −.318 | .378 | .707 | 1 | .400 | .728 | .347 | 1.526 |
| LDL_B | −.078 | .117 | .443 | 1 | .506 | .925 | .736 | 1.163 |
| LNINS | −.119 | .254 | .220 | 1 | .639 | .888 | .540 | 1.460 |
| current_smoker0 | .225 | .264 | .727 | 1 | .394 | 1.253 | .746 | 2.103 |
| pr_cv_2008 | −.414 | .979 | .179 | 1 | .672 | .661 | .097 | 4.502 |
| ZLN_PNT | .315 | .114 | 7.703 | 1 | .006 | 1.371 | 1.097 | 1.713 |

Variables in the Equationb

| | B | SE | Wald | df | Sig. | Exp(B) | 95.0% CI for Exp(B) Lower | Upper |
|---|---|---|---|---|---|---|---|---|
| SEX | | | . | 0a | . | | | |
| AGE | .007 | .022 | .102 | 1 | .750 | 1.007 | .965 | 1.051 |
| AHT_B | .208 | .276 | .568 | 1 | .451 | 1.232 | .717 | 2.117 |
| SBP_B | −.001 | .007 | .011 | 1 | .918 | .999 | .986 | 1.013 |
| WAIST_B | .057 | .021 | 7.100 | 1 | .008 | 1.059 | 1.015 | 1.104 |
| BMI_B | −.062 | .055 | 1.269 | 1 | .260 | .940 | .845 | 1.047 |
| GLUCOS_B | 2.359 | .296 | 63.676 | 1 | .000 | 10.578 | 5.927 | 18.881 |
| HDL_B | −.318 | .378 | .707 | 1 | .400 | .728 | .347 | 1.526 |
| LDL_B | −.078 | .117 | .443 | 1 | .506 | .925 | .736 | 1.163 |
| LNINS | −.119 | .254 | .220 | 1 | .639 | .888 | .540 | 1.460 |
| current_smoker0 | .225 | .264 | .727 | 1 | .394 | 1.253 | .746 | 2.103 |
| pr_cv_2008 | −.414 | .979 | .179 | 1 | .672 | .661 | .097 | 4.502 |
| ZLN_PNT | .315 | .114 | 7.703 | 1 | .006 | 1.371 | 1.097 | 1.713 | aDegree of freedom reduced because of constant or linearly dependent covariates
b. Constant or Linearly Dependent Covariates SEX = 2;

Among subjects free from impaired fasting glucose and diabetes mellitus at baseline 68 subjects developed new-onset diabetes during follow-up and after full adjustment for diabetes risk factors each SD increase of P-NT was associated with a hazard ration of 1.48 (1.17-1.87) (P=0.001) for the risk of new-onset diabetes mellitus in the whole population, 1.47 (1.08-2.00) (P=0.014) in women and 1.56 (1.08-2.27) (P=0.019) in men. Of all diabetes risk factors entered into the multivariate Cox regression model only baseline levels of fasting blood glucose had a stronger statistical relationship with new-onset diabetes mellitus than did P-NT.

Figure 2A:
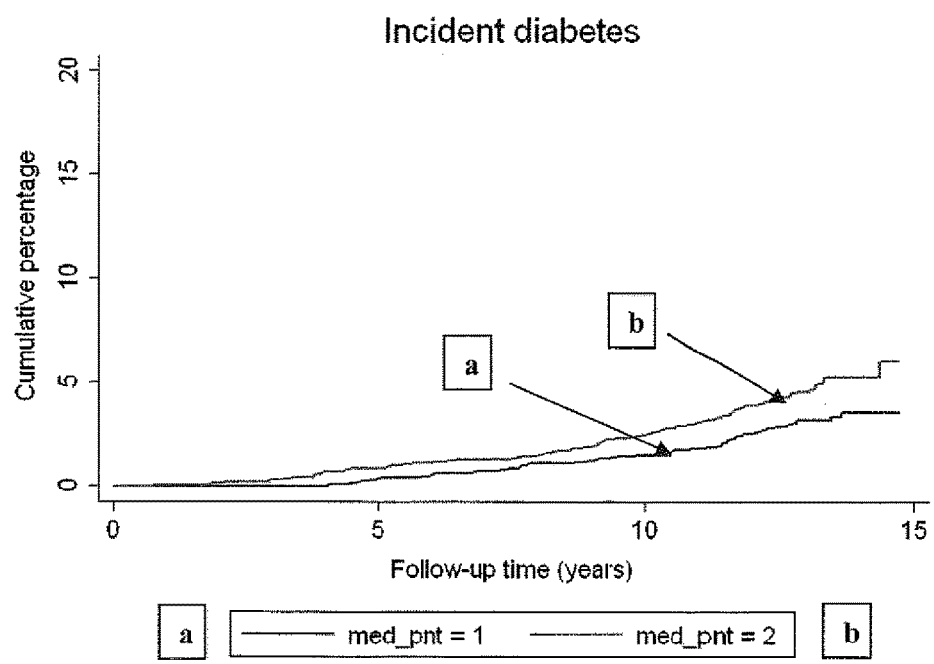
Figure 2B:
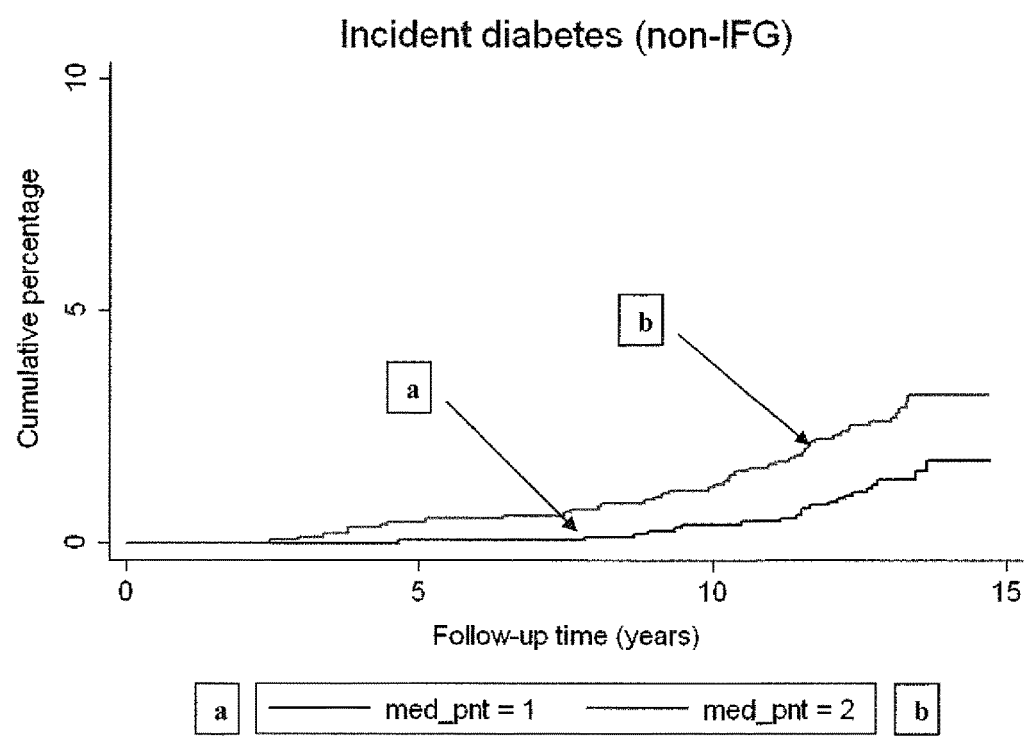

FIG. 2: Kaplan Meier analysis of diabetes prediction

2a) All subjects without diabetes using median cut off (104.6 pmol/l)

2b) All subjects without diabetes and pre-diabetes (IFG), cut off, (104.6 pmol/l)

Subgroup Analysis

Using the same variables in the equation, we investigated different subgroups for prediction of ID diabetes, subjects with diabetes at baseline were excluded.

TABLE 19

| Subgroup | No of subjects | No of events | Hazard risk per 1SD PNT | Significance (p-value) |
| --- | --- | --- | --- | --- |
| all | 3704 | 142 | 27.8% | 0.003 |
| all w/o non impaired fasting glucose | 3102 | 64 | 47.9 | 0.001 |
| females w/o non impaired fasting glucose | 1950 | 38 | 47% | 0.014 |

TABLE 19-continued

| Subgroup | No of subjects | No of events | Hazard risk per 1SD PNT | Significance (p-value) |
| --- | --- | --- | --- | --- |
| male w/o non impaired fasting glucose (IFG) | 1152 | 26 | 56.5% | 0.019 |
| HBP Women | 1318 | 53 | 52.5% | 0.002 |
| HBP women w/o non IFG | 1119 | 25 | 58.4% | 0.02 |
| Normotensive women | 1014 | 46 | 40.1% | 0.014 |
| Normotensive women w/o non IFG | 1014 | 12 | 125% | 0.001 |

P-NT is significantly predictive for diabetes development. The predictive power of P-NT was stronger in subjects without IFG (pre-diabetes).

FIGURE DESCRIPTION

FIG. 1 shows a typical P-NT dose/signal curve

FIG. 2: Kaplan Meier analysis of diabetes prediction

2a) All subjects without diabetes using median cut off (104.6 pmol/l)

2b) All subjects without diabetes and pre-diabetes (IFG), cut off, (104.6 pmol/l)

The invention claimed is:

1. A method comprising
contacting a sample of a bodily fluid from a fasting non-diabetic subject with a level pro-neurotensin 1-117 of 78 pmol/l or above with an antibody that binds to pro-neurotensin 1-117 and administering a dietary measure to reduce the fat uptake of said fasting non-diabetic subject to lower the risk of contracting diabetes mellitus and/or metabolic syndrome.

2. A method of claim 1 wherein the sample of bodily fluid is selected from the group consisting of a blood sample a plasma sample, a cerebrospinal fluid sample, a serum sample, a urine sample or an extract of the aforementioned samples.

3. A method according to claim 1, wherein the sample of bodily fluid is from a subject which is a fasting non-diabetic and non-prediabetic (non-IFG) subject.

4. A method according to claim 1, wherein the blood sample has a blood glucose level of less than 6.1 mmol/l but more than 5.4 mmol/l.

5. A method according to claim 1, wherein the blood sample has a blood glucose level of less than 5.4 mmol/l.

6. A method according to claim 1 wherein said antibody is full-length immunoglobulin, or fragments therein containing at least the F-variable domain of heavy and/or light chain.

7. A method according to claim 1 wherein the level of pro-neurotensin 1-117 in the bodily fluid is between 78-150 pmol/l.

8. A method according to claim 1 wherein the level of pro-neurotensin 1-117 in the bodily fluid is 78, 79, 80, 81, 82, 83, 84, 85, 86, 87, 88, 89, 90, 91, 92, 93, 94 95, 96 97 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149 or 150 pmol/l.

\* \* \* \* \*

SEQUENCE LISTING

```
<160> NUMBER OF SEQ ID NOS: 12

<210> SEQ ID NO 1
<211> LENGTH: 147
<212> TYPE: PRT
<213> ORGANISM: Homo sapiens

<400> SEQUENCE: 1

Ser Asp Ser Glu Glu Glu Met Lys Ala Leu Glu Ala Asp Phe Leu Thr
1               5                   10                  15

Asn Met His Thr Ser Lys Ile Ser Lys Ala His Val Pro Ser Trp Lys
            20                  25                  30

Met Thr Leu Leu Asn Val Cys Ser Leu Val Asn Asn Leu Asn Ser Pro
        35                  40                  45

Ala Glu Glu Thr Gly Glu Val His Glu Glu Glu Leu Val Ala Arg Arg
    50                  55                  60

Lys Leu Pro Thr Ala Leu Asp Gly Phe Ser Leu Glu Ala Met Leu Thr
65                  70                  75                  80

Ile Tyr Gln Leu His Lys Ile Cys His Ser Arg Ala Phe Gln His Trp
                85                  90                  95

Glu Leu Ile Gln Glu Asp Ile Leu Asp Thr Gly Asn Asp Lys Asn Gly
            100                 105                 110

Lys Glu Glu Val Ile Lys Arg Lys Ile Pro Tyr Ile Leu Lys Arg Gln
        115                 120                 125

Leu Tyr Glu Asn Lys Pro Arg Pro Tyr Ile Leu Lys Arg Asp Ser
    130                 135                 140

Tyr Tyr Tyr
145

<210> SEQ ID NO 2
<211> LENGTH: 125
<212> TYPE: PRT
<213> ORGANISM: Homo sapiens
```

<400> SEQUENCE: 2

Ser Asp Ser Glu Glu Met Lys Ala Leu Glu Ala Asp Phe Leu Thr
1               5                   10                  15

Asn Met His Thr Ser Lys Ile Ser Lys Ala His Val Pro Ser Trp Lys
            20                  25                  30

Met Thr Leu Leu Asn Val Cys Ser Leu Val Asn Asn Leu Asn Ser Pro
            35                  40                  45

Ala Glu Glu Thr Gly Glu Val His Glu Glu Leu Val Ala Arg Arg
    50                  55                  60

Lys Leu Pro Thr Ala Leu Asp Gly Phe Ser Leu Glu Ala Met Leu Thr
65                  70                  75                  80

Ile Tyr Gln Leu His Lys Ile Cys His Ser Arg Ala Phe Gln His Trp
                85                  90                  95

Glu Leu Ile Gln Glu Asp Ile Leu Asp Thr Gly Asn Asp Lys Asn Gly
            100                 105                 110

Lys Glu Glu Val Ile Lys Arg Lys Ile Pro Tyr Ile Leu
            115                 120                 125

<210> SEQ ID NO 3
<211> LENGTH: 6
<212> TYPE: PRT
<213> ORGANISM: Homo sapiens

<400> SEQUENCE: 3

Lys Ile Pro Tyr Ile Leu
1               5

<210> SEQ ID NO 4
<211> LENGTH: 13
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: pyroQ

<400> SEQUENCE: 4

Xaa Leu Tyr Glu Asn Lys Pro Arg Arg Pro Tyr Ile Leu
1               5                   10

<210> SEQ ID NO 5
<211> LENGTH: 117
<212> TYPE: PRT
<213> ORGANISM: Homo sapiens

<400> SEQUENCE: 5

Ser Asp Ser Glu Glu Met Lys Ala Leu Glu Ala Asp Phe Leu Thr
1               5                   10                  15

Asn Met His Thr Ser Lys Ile Ser Lys Ala His Val Pro Ser Trp Lys
            20                  25                  30

Met Thr Leu Leu Asn Val Cys Ser Leu Val Asn Asn Leu Asn Ser Pro
            35                  40                  45

Ala Glu Glu Thr Gly Glu Val His Glu Glu Leu Val Ala Arg Arg
    50                  55                  60

Lys Leu Pro Thr Ala Leu Asp Gly Phe Ser Leu Glu Ala Met Leu Thr
65                  70                  75                  80

Ile Tyr Gln Leu His Lys Ile Cys His Ser Arg Ala Phe Gln His Trp
                85                  90                  95

```
Glu Leu Ile Gln Glu Asp Ile Leu Asp Thr Gly Asn Asp Lys Asn Gly
            100                 105                 110

Lys Glu Glu Val Ile
        115
```

<210> SEQ ID NO 6
<211> LENGTH: 132
<212> TYPE: PRT
<213> ORGANISM: Homo sapiens

<400> SEQUENCE: 6

```
Ser Asp Ser Glu Glu Met Lys Ala Leu Glu Ala Asp Phe Leu Thr
1               5                   10                  15

Asn Met His Thr Ser Lys Ile Ser Lys Ala His Val Pro Ser Trp Lys
            20                  25                  30

Met Thr Leu Leu Asn Val Cys Ser Leu Val Asn Asn Leu Asn Ser Pro
        35                  40                  45

Ala Glu Glu Thr Gly Glu Val His Glu Glu Leu Val Ala Arg Arg
    50                  55                  60

Lys Leu Pro Thr Ala Leu Asp Gly Phe Ser Leu Glu Ala Met Leu Thr
65                  70                  75                  80

Ile Tyr Gln Leu His Lys Ile Cys His Ser Arg Ala Phe Gln His Trp
                85                  90                  95

Glu Leu Ile Gln Glu Asp Ile Leu Asp Thr Gly Asn Asp Lys Asn Gly
            100                 105                 110

Lys Glu Glu Val Ile Lys Arg Lys Ile Pro Tyr Ile Leu Lys Arg Gln
        115                 120                 125

Leu Tyr Glu Asn
    130
```

<210> SEQ ID NO 7
<211> LENGTH: 125
<212> TYPE: PRT
<213> ORGANISM: Homo sapiens

<400> SEQUENCE: 7

```
Ser Asp Ser Glu Glu Met Lys Ala Leu Glu Ala Asp Phe Leu Thr
1               5                   10                  15

Asn Met His Thr Ser Lys Ile Ser Lys Ala His Val Pro Ser Trp Lys
            20                  25                  30

Met Thr Leu Leu Asn Val Cys Ser Leu Val Asn Asn Leu Asn Ser Pro
        35                  40                  45

Ala Glu Glu Thr Gly Glu Val His Glu Glu Leu Val Ala Arg Arg
    50                  55                  60

Lys Leu Pro Thr Ala Leu Asp Gly Phe Ser Leu Glu Ala Met Leu Thr
65                  70                  75                  80

Ile Tyr Gln Leu His Lys Ile Cys His Ser Arg Ala Phe Gln His Trp
                85                  90                  95

Glu Leu Ile Gln Glu Asp Ile Leu Asp Thr Gly Asn Asp Lys Asn Gly
            100                 105                 110

Lys Glu Glu Val Ile Lys Arg Lys Ile Pro Tyr Ile Leu
        115                 120                 125
```

<210> SEQ ID NO 8
<211> LENGTH: 21
<212> TYPE: PRT
<213> ORGANISM: Homo sapiens

```
<400> SEQUENCE: 8

Lys Ile Pro Tyr Ile Leu Lys Arg Gln Leu Tyr Glu Asn Lys Pro Arg
1               5                   10                  15

Arg Pro Tyr Ile Leu
            20

<210> SEQ ID NO 9
<211> LENGTH: 28
<212> TYPE: PRT
<213> ORGANISM: Homo sapiens

<400> SEQUENCE: 9

Lys Ile Pro Tyr Ile Leu Lys Arg Gln Leu Tyr Glu Asn Lys Pro Arg
1               5                   10                  15

Arg Pro Tyr Ile Leu Lys Arg Asp Ser Tyr Tyr Tyr
            20                  25

<210> SEQ ID NO 10
<211> LENGTH: 20
<212> TYPE: PRT
<213> ORGANISM: Homo sapiens

<400> SEQUENCE: 10

Gln Leu Tyr Glu Asn Lys Pro Arg Arg Pro Tyr Ile Leu Lys Arg Asp
1               5                   10                  15

Ser Tyr Tyr Tyr
            20

<210> SEQ ID NO 11
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Cys Ser Asp Ser Glu Glu Glu Met Lys Ala Leu Glu Ala Asp Phe Leu
1               5                   10                  15

Thr Asn Met His
            20

<210> SEQ ID NO 12
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Cys Asn Leu Asn Ser Pro Ala Glu Glu Thr Gly Glu Val His Glu Glu
1               5                   10                  15

Glu Leu Val Ala
            20
```